United States Patent
Simonis (10) Patent No.: US 9,878,084 B2
(45) Date of Patent: Jan. 30, 2018

(54) REDOX CONTROLLED ELECTROSORPTION AND DECOMPOSITION DEVICE FOR THE PURIFICATION OF BLOOD AND OTHER FLUIDS

(71) Applicant: ICINNOVATION BV, Oirschot (NL)

(72) Inventor: Frank Simonis, Oirschot (NL)

(73) Assignee: ICINNOVATION BV, Oirschot (NL)

( * ) Notice: Subject to any disclaimer, the term of this patent is extended or adjusted under 35 U.S.C. 154(b) by 66 days.

(21) Appl. No.: 15/030,660

(22) PCT Filed: Oct. 17, 2014

(86) PCT No.: PCT/NL2014/050729
§ 371 (c)(1),
(2) Date: Apr. 20, 2016

(87) PCT Pub. No.: WO2015/060716
PCT Pub. Date: Apr. 30, 2015

(65) Prior Publication Data
US 2016/0250404 A1 Sep. 1, 2016

(30) Foreign Application Priority Data

Oct. 21, 2013 (EP) .................................. 13189604

(51) Int. Cl.
*A61M 1/16* (2006.01)
*A61M 1/28* (2006.01)
(Continued)

(52) U.S. Cl.
CPC ........ *A61M 1/1621* (2014.02); *A61M 1/1656* (2013.01); *A61M 1/1696* (2013.01);
(Continued)

(58) Field of Classification Search
CPC .............. A61M 1/1621; A61M 1/1656; A61M 1/1696; A61M 1/28; A61M 1/284;
(Continued)

(56) References Cited

U.S. PATENT DOCUMENTS

| 3,878,564 A | 4/1975 | Yao et al. |
|---|---|---|
| 4,473,449 A | 9/1984 | Michaels et al. |

(Continued)

FOREIGN PATENT DOCUMENTS

| DE | 196 40 839 A1 | 4/1998 |
|---|---|---|
| EP | 0 577 026 A2 | 1/1994 |

(Continued)

OTHER PUBLICATIONS

International Search Report, dated Mar. 31, 2015, from corresponding PCT application.

*Primary Examiner* — John Kim
(74) *Attorney, Agent, or Firm* — Young & Thompson (57) ABSTRACT

Device for removing substances from blood and other fluids such as water, wastewater, chemicals and other biofluids, includes i) an electrocatalytic decomposition filter including a DC power source, a set of electrodes with a catalytic surface or in direct contact with sorbents offering catalytic activity, ii) an electrosorption filter including a DC power source, a set of electrodes, nanostructured sorption material and/or a porous polymer matrix, iii) an inlet for entry of blood or blood plasma or dialysate fluid into the device, iv) an outlet for the removal of purified blood, blood plasma, ultrafiltrate or dialysate fluid from the device, and v) a conduit connecting the inlet with the outlet and holding the electrosorption filter such that the blood, blood plasma, ultrafiltrate or dialysate fluid is forced through the elec- (Continued)

trosorption and electrocatalytic decomposition filter, and vi) a sensor and control system to safeguard the device from producing oxidative stress.

18 Claims, 5 Drawing Sheets

(51) Int. Cl.
- *A61M 1/34* (2006.01)
- *B01D 15/20* (2006.01)
- *B01D 15/36* (2006.01)
- *B01D 15/38* (2006.01)
- *B01D 19/00* (2006.01)
- *B01D 61/24* (2006.01)
- *B01D 61/32* (2006.01)
- *A61M 1/36* (2006.01)
- *C02F 1/467* (2006.01)
- *C02F 1/469* (2006.01)
- *C02F 1/28* (2006.01)
- *C02F 1/42* (2006.01)
- *C02F 1/66* (2006.01)
- *C02F 1/70* (2006.01)
- *C02F 1/461* (2006.01)
- *C02F 101/16* (2006.01)
- *C02F 101/38* (2006.01)
- *C02F 103/02* (2006.01)
- *C02F 103/20* (2006.01)

(52) U.S. Cl.
CPC .............. *A61M 1/28* (2013.01); *A61M 1/284* (2014.02); *A61M 1/3472* (2013.01); *A61M 1/3496* (2013.01); *A61M 1/3679* (2013.01); *B01D 15/203* (2013.01); *B01D 15/361* (2013.01); *B01D 15/3885* (2013.01); *B01D 19/0084* (2013.01); *B01D 61/243* (2013.01); *B01D 61/32* (2013.01); *C02F 1/469* (2013.01); *C02F 1/4672* (2013.01); *A61M 1/3687* (2013.01); *A61M 2205/7554* (2013.01); *B01D 2311/246* (2013.01); *B01D 2311/2623* (2013.01); *B01D 2311/2626* (2013.01); *B01D 2311/2634* (2013.01); *B01D 2311/2684* (2013.01); *B01D 2311/2696* (2013.01); *B01D 2313/345* (2013.01); *B01D 2313/40* (2013.01); *B01D 2313/90* (2013.01); *C02F 1/281* (2013.01); *C02F 1/283* (2013.01); *C02F 1/285* (2013.01); *C02F 1/42* (2013.01); *C02F 1/66* (2013.01); *C02F 1/70* (2013.01); *C02F 2001/46142* (2013.01); *C02F 2101/16* (2013.01); *C02F 2101/38* (2013.01); *C02F 2103/026* (2013.01); *C02F 2103/20* (2013.01); *C02F 2201/006* (2013.01); *C02F 2201/4613* (2013.01); *C02F 2201/46135* (2013.01); *C02F 2209/02* (2013.01); *C02F 2209/04* (2013.01); *C02F 2209/05* (2013.01); *C02F 2209/06* (2013.01); *C02F 2303/16* (2013.01); *C02F 2305/08* (2013.01)

(58) Field of Classification Search
CPC .............. A61M 1/3472; A61M 1/3496; A61M 1/3679; A61M 1/3687; A61M 2205/7554; B01D 15/203; B01D 15/361; B01D 15/3885; B01D 19/0084; B01D 2311/246; B01D 2311/2623; B01D 2311/2626; B01D 2311/2634; B01D 2311/2684; B01D 2311/2696; B01D 2313/345; B01D 2313/40; B01D 2313/90; B01D 61/243; B01D 61/32; C02F 1/281; C02F 1/283; C02F 1/285; C02F 1/42; C02F 1/4672; C02F 1/469; C02F 1/66; C02F 1/70; C02F 2001/46142; C02F 2101/16; C02F 2101/38; C02F 2103/026; C02F 2103/20; C02F 2201/006; C02F 2201/4613; C02F 2201/46135; C02F 2209/02; C02F 2209/04; C02F 2209/05; C02F 2209/06; C02F 2303/16; C02F 2305/08

See application file for complete search history.

(56) References Cited

U.S. PATENT DOCUMENTS

| | | |
|---|---|---|
| 6,051,188 A | 4/2000 | Spickermann |
| 2003/0097086 A1 | 5/2003 | Gura |
| 2007/0284313 A1 | 12/2007 | Lee et al. |

FOREIGN PATENT DOCUMENTS

| | | |
|---|---|---|
| EP | 2 092 944 A2 | 8/2009 |
| GB | 1 406 133 A | 9/1975 |
| WO | 03020403 A1 | 3/2003 |
| WO | 2012/060700 A1 | 5/2012 |

REDOX CONTROLLED ELECTROSORPTION AND DECOMPOSITION DEVICE FOR THE PURIFICATION OF BLOOD AND OTHER FLUIDS

FIELD OF THE INVENTION

The present invention relates to a device for the removal of toxic substances from dialysate fluid, blood, blood plasma or ultra filtrate, comprising:
i) a housing having an inlet for entry of dialysate fluid, blood, blood plasma or ultrafiltrate into said housing, an outlet for the removal of purified dialysate fluid, blood, blood plasma or ultrafiltrate and excess fluid from said housing, and a conduit connecting said inlet with said outlet
ii) an electrocatalytic decomposition filter for removing toxins, toxic solutes, toxic small and middle-sized molecules and protein bound toxins from the dialysate fluid, blood, bloodplasma or ultrafiltrate, said electrocatalytic decomposition filter being contained in said conduit such that said dialysate fluid, blood, blood plasma or ultrafiltrate must pass through said electrocatalytic decomposition filter when flowing from said inlet to said outlet and said electrocatalytic decomposition filter comprising:
   a) a set of electrodes with an electrocatalytic surface for decomposition and gasification of toxins via electrooxidation;
   b) or a set of electrodes that are in direct electrical contact with porous materials that have been coated with elecrocatalytic material;
   c) power source to provide the electrodes with an electrical charge in order to activate the electrocatalytic electrode surface;
   d) an electronic means to control and switch the electrical charge on the electrodes in view of resorbing and release of toxins and to prevent built-up of deposits on the electrodes,
iii) an electrosorption filter for removing toxins, toxic solutes, toxic small and middle-sized molecules and protein bound toxins from the dialysate fluid, blood, bloodplasma or ultrafiltrate, said electrosorption filter being contained in said conduit such that said dialysate fluid, blood, blood plasma or ultrafiltrate must pass through said electrosorption filter when flowing from said inlet to said outlet and said electrosorption filter comprising:
   a) a nanostructured sorption material;
   b) a set of electrodes coated with or in electrical contact with the sorption material;
   c) a power source to provide the electrodes with an electrical charge and generate an electrical field strength in the sorption medium.
   d) a sensor unit for monitoring the quality of the cleansed fluid and a control system to correct and adjust the quality of the cleansed fluid.

The invention relates to a stand-alone device for the removal of toxic substances from a biofluid, such as from the blood from a patient, to methods of removing toxic substances from blood using the inventive device in a wearable unit enabling continuous blood purification while being mobile. The invention is also applicable to other fluids such as (waste) water, process chemicals and other biofluids such as removing substances from urine, dialysate fluids, milk, biochemical analysis and processing fluids. Specific measures are taken to secure the biocompatibility of the cleansed fluid and to prevent oxidative stress. In a reverse mode the invented system can be used to release ingredients in a controlled manner.

BACKGROUND OF THE INVENTION

Hemodialysis (HD) and peritoneal dialysis (PD) are methods of removing toxic substances (impurities or wastes) from the blood when the kidneys are unable to do so sufficiently. Dialysis is most frequently used for patients who have kidney failure, but may also be used to quickly remove drugs or poisons in acute situations. This technique can be life saving in people with acute or chronic kidney failure. Best known is hemodialysis, which works by circulating the blood along special filters outside the body in a dialysis machine. Here, the blood flows across a semipermeable membrane (the dialyser or filter), on the other side of which flows a dialysis fluid in a counter-current direction to the blood flow. The dialysing membrane allows passage of substances below a certain molecular cut-off. By diffusion the concentration of these substances will end up being the same on both sides of the membrane. The dialysis fluid removes the toxins from the blood and is generally discarded as waste dialysate. The chemical imbalances and impurities of the blood are being brought back in minimal balance and the blood is then returned to the body. The efficacy of hemodialysis is 10-15%, which means that 10-15% of the toxins are being removed from the blood. Typically, most patients undergo hemodialysis for three sessions every week. Each session lasts normally 3-4 hours. This is very inconvenient, and the physical and social side effects of dialysis to the patients are a great concern.

In order to provide for portable dialysis devices, that will allow patients to engage in normal daily activities, artificial kidneys have been developed. Essentially there are two types of artificial kidneys.

In one form, the principle of the artificial kidney consists of extracting urea and other more toxic middle molecules from blood by dialysis and regeneration of the dialysate by means of an adsorbent, usually activated carbon. In the case of a system based on such a dialysis kidney machine, a key aspect resides in regenerating the dialysis fluid when the latter is to be recycled into the dialyser. Dialysis kidney machines that can be encountered in the prior art include for instance those described in GB1406133, and US 2003/0097086. GB1406133 discloses an artificial kidney of the recycle type having an improved adsorbent comprising activated carbon and alumina. US 2003/0097086 discloses a portable dialysis device comprising dialyzers connected in series that utilize dialysate, and further comprising a plurality of contoured sorbent devices, which are connected in series and are for regenerating the spent dialysate. As adsorption materials for regeneration of the spent dialysate, activated charcoal, urease, zirconium phosphate, hydrous zirconium oxide and/or activated carbon are provided.

In another form, the principle of the artificial kidney may be based on ultrafiltration, or hemofiltration, using appropriate membranes, wherein large molecules including blood cells are retained in the retentate on the filter, and the toxic substances are collected in the (ultra)filtrate. During hemofiltration, a patient's blood is passed through a set of tubing (a filtration circuit) via a machine to a semipermeable membrane (the filter) where waste products and water are removed. Replacement fluid is added and the blood is returned to the patient. In a similar fashion to dialysis, hemofiltration involves the movement of solutes across a semi-permeable membrane. However, the membrane used in hemofiltration is far more porous than that used in hemodialysis, and no dialysate is used-instead a positive hydrostatic pressure drives water and solutes across the filter membrane where they are drained away as filtrate. An isotonic replacement fluid is added to the resultant filtered blood to replace fluid volume and valuable electrolytes. This is then returned to the patient. Thus, in the case of ultrafiltration, a key aspect resides in separating the urea from the other components in the ultrafiltrate such as salts which have also passed through the membrane but which must be reincorporated into the blood in order to maintain the electrolyte composition thereof substantially constant.

Another approach relates to electrodialysis, a method to fasten the dialysis process by applying an electrical field over the dialysate membrane similar to electrophoresis systems. For instance in WO03020403 a dialysate system is proposed with an electrical voltage over the membrane. The proposed voltage is in the range of 50-150 Volts. It is claimed that the electrical field promotes the diffusion rate and hereby the clearance rate of toxins such as small solutes, phosphate, creatinine, beta2microglobuline and even urea. A major drawback however is the required high voltage resulting in significant heating of the blood. This system therefore requires an additional cooling section making the system bulky and energy consuming.

Another relevant approach is known from purification of water and is called electrosorption. E.g. in US2007284313 an apparatus is disclosed for removing inorganic ions such as salt and metals from water by means of carbon electrodes that are activated with a small voltage. This system seems to work well for water and inorganic substances. Nothing has been disclosed so far for removing organic molecules and substances such as toxic small and middle molecules and proteins via electrosorption.

In conclusion, the prior art discloses both dialysing and ultrafiltration devices, wherein various substances may be used as sorbents. Also the use of an external electrical field to boost the dialysate diffusion process has been disclosed.

The problem with the system of the prior art is that however, that they are still too large due to limited sorption capacity of the materials, or not efficient or both, in order to allow small, desk-top sized or wearable blood purification systems.

Removing toxins from blood and tissue via electrical activated oxidation has been described already in 1975 e.g. in U.S. Pat. No. 3,878,564. In 1982, in particular U.S. Pat. No. 4,473,449, such a process has been described for the regeneration of dialysate fluid using Pt, Ti with $TiO_2$, $SnO_2$ or $RuO_2$ coatings as electrode materials. This process has never been applied nor practiced in blood purification, most likely because the process produces unwanted oxidation products such as chloramines.

Removing toxins via an electrosorption device has been well described in patent EP2092944 published in 2009. Although the proposed technology is regarded as an important step forward in blood purification, the removal of urea is still problematic and requires a relatively high volume and mass of sorbents. An electrosorption and decomposition system according to the preamble of claim 1 is known from WO2012060700A. This known system combines electrosorption of electrolytes and electrocatalytical decomposition of organic toxins such as urea by means a sorbent unit comprising sorbents and electrodes. This approach has been tested with very good results. However additional safety measures are needed in order to secure the quality of the cleansed fluid, especially with respect to the prevention of oxidative stress. Oxidative stress may occur due to the formation of unwanted byproducts such as chloramines during the electrocatalytic decomposition. Prevention of oxidative stress is paramount for a safe and biocompatible operation.

It is an object of the present invention to overcome the potential problems with oxidative stress and to provide a compact and efficient sorption-filter and decomposition system with inbuilt measures to prevent oxidative stress for use in hemodialysis, peritoneal dialysis systems and—more genericly—for use in blood purification systems such as a wearable artificial kidney, artificial liver, artficial lung etc. In similar form such a system is applicable for purification of other fluids such as the purification of water, waste water treatment and purification of e.g. aquarium water.

SUMMARY OF THE INVENTION

This problem is solved according to the invention by providing a device characterised in that the sensor unit is a sensor unit for monitoring the redox state the electrocatalytic decomposition rate of the cleansed fluid and the control system controls infusion of a reducing agent to correct and adjust the cleansed fluid to prevent oxidative stress wherein the electrodes are made from carbonaceous material.

Said toxic substances are preferably selected from potassium, phosphate, urea, uric acid, ammonia, creatinine, beta2-microglobulin ($\square$2M), and albumin-bound toxins such as paramino hyppuric acid, p-cresol, indoxyl sulphate, CMPF and bilirubin The electrosorption filter combines nanostructured sorbent materials with a high specific and selective surface area together with additional electric surface charging delivered by an external power source. This combination enables a very efficient, highly effective and therefore small sized sorption system. The combination with a filter with electrodes that provide electrocatalytic decomposition of urea, urate, ammonia, creatinine and other components with amine-groups provide that these toxins can be removed via gasification in stead of absorption, reducing the amount of sorbents that are needed considerably. This enfavours a strong reduction in size of the device. Possibly unwanted oxidation products arising from this electrocatalytic decomposition process such as partly oxidized aminoacids, peptides and proteins as well as unwanted residues from the electrocatalytic decomposition such as chloramines and chlorine are being removed effectively by the electrosorption filter. The electrosorption filter and the electrocatalytic decomposition filter therefore operate in a very synergetic mode: the electrocatalytic decomposition filter enables a strong reduction of the volume of the sorbents in the electrosorption filter, whereas the electrosorption filter removes the resulting uremic toxins and unwanted by-products from the electrocatalytic decomposition filter. The electrosorption filter and the electrocatalytic decomposition filter can ideally be integrated into one electrosorption/decomposition system wherein the electrodes of the electrosorption filter are made of electrocatalytic decomposition material. The electrosorption and electrocatalytic breakdown process are than combined. This allows a further reduction in size and weight. Another important feature of such a combined setup is that the sorption materials are continuously exposed to the electro-catalytic decomposition process. This prevents that sorption materials are being clogged with organic deposites such as proteins.

In order to secure a safe and biocompatible operation of the device, the removal of unwanted residues such as chloramines is being measured and controlled by means of a sensor (i.c. a redox sensor) and a control mechanism to adjust the intensity of the electrocatalytic decomposition. Herewith the oxidation state of the cleansed fluid can be kept within biocompatible limits (<0.1 mg/l chloramines). In case of a sudden breakthrough of chloramines, a second action is taken and an injector system is activated to inject a fluid with a reducing agent e.g. vitamin C, vitamin E or glutathione in order to neutralize the oxidative chloramines.

The small size and subsequent low weight allows for a small, desk-top size system and even a wearable device for water treatment, blood filtration or hemodialysis or peritoneal dialysis is feasible.

Said electrosorption filter comprises an absorbing, adsorption, ion-exchange and/or surface crystallisation material with very small nano sized particles or pores offering a large specific surface area in combination with a high chemical surface activity like activated carbon, ion-exchange resins (e.g. ps-pvb based), nanoclays, nanocrystalline hydrotalcites, nanoporous silica's, nanoporous or layered alumina silicates (like zeolites), nanoporous metal oxides and metal hydroxides, metal organic frameworks, zeolite imidazolate frameworks, nanosized and/or activated graphite, cyclo-dextrines, crystallisation seeds, a highly porous matrix material with again a large specific surface area, with tunable porosity and a high specific chemical activity like carboxymethyl cellulose and like a biopolymer such as oxidized starch modified with functional groups for specific absorption or combinations thereof.

The redox sensor is used to regulate the electrocatalytic decomposition power and to activate an injector for the injection of reducing or oxidizing agents in case of an emergency. This injector can also be applied to inject medicine or substances to control the pH (e.g. bicarbonate).

A further embodiment of the device according to the invention is characterized in that said device further comprises a plasmafilter for separating patient blood plasma from patient blood cells.

A further embodiment of the device according to the invention is characterized in that said device further comprises a hemofilter for separating blood ultrafiltrate from the patients blood, wherein the ultrafiltrate is being separated from blood cells, platelets and large (typically >50 kDa) molecules such as albumine, protein S and C and LDL-cholesterol.

In this embodiment said sorption-filter is combined with a plasma- or hemofilter system in order to form an artificial kidney device for the removal of toxic substances from the blood from a patient, comprising a plasmafilter for separating patient blood plasma from patient blood cells, or a hemofilter to separate blood ultrafiltrate from the patient blood, electrodes in combination with a sorption-filter for removing toxins, toxic small- and middle-sized molecules and protein bound toxins from the patient blood plasma and optionally to supplement the blood with at least one substance selected from the group consisting of vitamins, minerals, anticoagulants, anti microbial agents and other medicaments and electrodes made from or coated with catalytic material for the decomposition and gasification of urea, urate, ammonia and other components with amine-groups.

In case of blood filtration, a plasmafilter for separating patient's blood plasma from the blood or a hemofilter for separating patient's blood ultrafiltrate from the blood is used followed by the electrosorption and decomposition filter for removing toxic ionic solutes, toxic small- and middle-sized molecules and protein bound toxins from the patient's blood plasma or ultrafiltrate.

In yet another preferred embodiment said device is part of a hemodialysis or peritoneal dialysis system in order to improve the absorption capacity of the dialysis fluid or to regenerate the dialysate in situ via said electrosorption and decomposition filter and hereby minimizing the dialysate fluid volume and the dimensions of the dialysate system, thereby allowing the dialysis system to be wearable.

In yet another preferred embodiment said dialysis system is a wearable dialysis system.

In a further preferred embodiment said plasmafilter or hemofilter comprises at least a further outlet for recovery of patient blood cells.

The sorption material can also be regenerated by operating the device in reversed mode, with a voltage reversal on the electrodes leading to a repulsion of bound toxins.

The regeneration of sorbents can also be achieved by flushing the sorbents with a regeneration fluid that will promote reversed ion-exchange and subsequent release of toxins. Such a regeneration fluid may consists of a water solution with specific salts, such as NaCl solution (typical concentration 0.5-10 wt %) or other sodium salts. The regeneration fluid might also contain other salts (preferably chlorides) from calcium, magnesium, iron or other components such as vitamins, EPO and medicine. Hereby the sorbents cannot only be regenerated but also be preloaded with components. These components will then be released to the blood system in normal use. This preloading is also of use in order to neutralise unwanted uptake of specific components by the sorbents.

The regeneration of sorbents can also be promoted by a reversed electrode mode operation in combination with a regeneration fluid.

Reversal of the voltage on the electrodes for the electrocatalytic decomposition is needed in order avoid inactivation due to electro-deposition of components from the fluid. The frequency for voltage reversal is not very critical and can vary from switching every second to switching every 0.1-20 hours.

Preferably the voltage of the external source is electronically regulated depending on the reading of the sensor system, especially the redox sensor.

BRIEF DESCRIPTION OF THE DRAWINGS

FIG. 1 shows a schematic setup of the fluidic system for a hemodialysis application. Blood of a patient is being purified via a dialysis procedure using a hemofilter and a dialysate circuit. The dialysate in the circuit is being continuously purified by a sorbent unit equipped with sorbents and electrodes for electrosorption and electrocatalytical decomposition. Dimensions of the sorbent unit are in the range of 100-1000 ml, typically around 200 ml. The volume of the dialysate is in the range of 50-500 ml, typically 100 ml. The weight of the dialysate and sorbent unit together are in the range of 150-1500 grams, typically 300 grams. After saturation with toxins, the sorbent unit can be regenerated by flushing with a saline or other sodium salt solution in order to remove the toxins. The frequency hereof depends on the size of the patient and the size of the sorbent unit, typically 1-4 times a day. A sensor and control system is provided in order to secure the quality of the dialysate. In order to safeguard the patient from oxidative stress, the redox state of the dialysate is continuously measured and based here on the intensity of the electrochemical decomposition is being adjusted. As a second safety measure, an injector system with a reducing agent such as vitamin C can be activated in case of an emergency. This injector system can also be used to infuse medicine or compounds such as bicarbonate to correct the acidose of the patient.

FIG. 2 shows a prototype version of a wearable hemodialysis device based upon the invention. It contains a hemofilter, blood pump, dialysate pump, various sensors to monitor the quality of the dialysate (temperature, pressure, conductivity, pH and redox), the sorbent unit with electrosorption and electrocatalytic decomposition and a degaser.

DETAILED DESCRIPTION OF THE INVENTION

The term "sorption" as used herein, refers to both adsorption and absorption. Adsorption is a process that occurs when a gas or liquid or solute (called adsorbate) accumulates on the surface of a solid or more rarely a liquid (adsorbent), forming a molecular or atomic film (adsorbate). It is different from absorption, where a substance diffuses into a liquid or solid to form a "solution". The term sorption encompasses both processes, while desorption is the reverse process.

The term "small-sized molecules", as used herein, refers to molecules with a molecular weight lower than 500 Da, such as uric acid, urea, guanidine, ADMA, creatinine.

The term "middle-sized molecules", as used herein, refers to molecules with a molecular weight between 500 Da and 5000 Da, such as end products from peptides and lipids, amines, amino acids, protein bound compounds, cytokines, leptins, microglobulins and some hormones.

The term "nanoporous materials" refers to materials having pores that are by definition roughly in the nanometer range, that is between $1 \times 10^{-7}$ and $0.2 \times 10^{-9}$ m and includes reference to the 3 categories set out by IUPAC of microporous materials (such as zeolites) having pore sizes of 0.2-2 nm; mesoporous materials having pore sizes of 2-50 nm; and macroporous materials having pore sizes of 50-1000 nm.

The term "ionic solutes", as used herein, refers to components such as phosphates, sulphates, carbon hydrates, chlorides, ammonia, potassium, calcium, sodium.

"Nano sized" as used herein, refers to a size of approximately 1-1000 nm, more preferably 1-100 nm.

The term "electrosorption" refers to a process where ionic solutes and charged molecules in a solution are being adsorbed onto the surface of a sorbent with the help of an additional electrical surface charge on the sorbent provided by an electrical power source.

The term "electrosorption filter" refers to a filter system comprising a sorbent that can be electrically charged or discharged with an external power source via electrodes connected to the sorbent material.

The term "catalytic" as used herein, refers to a process that specific chemical reactions are being promoted when in contact with another material due to specific inter-molecular interactions.

The term "electrocatalytic" as used herein refers to a catalytic chemical reaction that is being initiated via electrical activation.

The term "decomposition" as used herein refers to a chemical reaction where a component is broken down to its smaller constituents.

The term "gasification" as used herein refers to a chemical reaction where the component is being gasified and released from the system.

The term "electrocatalytic decomposition" as used herein refers to a process where a chemical component is being broken down into smaller chemical species, preferably gaseous species, via electrocatalytic oxidation.

The term "electrocatalytic decomposition filter" as used herein refers to a filter system comprising electrodes that remove toxins via electrocatalytic activated decomposition of these toxins and subsequent gasification.

The term "electrosorption-decomposition filter" as used herein refers to a filter system that combines an electrosorption filter and an electrocatalytic decomposition filter.

The Purification Device Holding an Electrosorption and Decomposition Filter Package A device of the present invention can take the form of an electrosorption and decomposition filter package that is placed in the dialysis fluid system of a hemodialysis or peritoneal dialysis system, enabling the removal of toxins from the dialysis fluid. The electrosorption and decomposition filter continuously purifies the dialysate fluid, keeping the toxin concentration in the dialysis fluid low, resulting in an improvement of the hemodialysis and peritoneal dialysis efficiency, typically with 100%, and reduces the consumption of dialysis fluid needed dramatically, ideally down to 0.1-1 liters. An additional and optional function of the sorption filter is to release ingredients for supplementing of the blood such as calcium, vitamin A, C and B12, anti-coagulation agents, anti microbial agents, minerals, specific medicaments etc. This option will simplify the operation of existing hemodialysis and peritoneal dialysis systems and will reduce the chance on occurring infections in the peritoneal dialysis system. Infusion of ingredients, supplements or medicaments can also be delivered by the injector system which is part of the redox state control system.

A device of the present invention can take the form of wearable peritoneal dialysis system wherein the electrosorption and decomposition filter package is placed in a wearable peritoneal dialysis system. Due to the continuous filtering of the electrosorption and decomposition filter, the volume of dialysate fluid can be reduced to typically 1-2 liters. The wearable peritoneal dialysis device comprises a tubular access system to the abdominal cavity and a unit comprising a fluid pump, power, sensors, electronic control, a facility to place and replace said electrosorption and decomposition filter package, typically on a daily basis and a system to dispose off excess water. The injector system of the redox control unit can be used to infuse continuously glucose in the peritoneal fluid in order to maintain osmotic pressure for extracting fluid from the patient. This may lower the overall glucose concentration needed and this in turn may enfavour the condition and lifetime of the patients peritoneal membrane.

A device of the present invention can take the form of wearable hemodialysis system wherein the electrosorption and decomposition filter system is placed in a wearable hemodialysis system. Thanks to the continuous filtering of the electrosorption and decomposition filter, the volume of dialysate fluid can be reduced to typically 50-500 ml. The wearable hemodialysis device comprises a vascular access tubing system and a unit comprising a small hemofilter system, fluid pump, power, sensors, electronic control, a facility to place and replace said electrosorption and decomposition filter package, typically on a daily-to-weekly basis, and a system to dispose off excess water. An additional and optional function of the device is to release ingredients for supplementing the blood such as calcium, vitamin A, anticoagulation agents, anti microbial agents, minerals, specific medicaments etc. This option will simplify the operation of the hemodialysis system and will reduce the chance on occurring infections.

d) A device of the present invention can take the form of a wearable or desktop sized artificial kidney based on blood plasmafiltration or blood ultrafiltration combined with electrosorption and decomposition filtering. In such an embodiment, the blood plasma filtration step will performed by a special plasma filter, or the ultrafiltrate will be extracted via a special hemofilter, with a relative large pore size, that separates blood from plasma or the ultrafiltrate, allowing toxic solutes, small/middle molecules and protein bound toxins to pass with the plasma or ultrafiltrate into the compartment with the electrosorption-decomposition filter package for cleansing. Via an additional hemofilter with a smaller pore size, excess water can be removed from the blood plasma or ultrafiltrate preventing loss of albumin. The cleansed blood plasma or ultrafiltrate is then re-entered into the bloodstream. It will be understood that in such an embodiment, the device further comprises the necessary tubing, vascular access and feedback systems, pumping, electronics, sensors, power packs and other requirements. However, these are not essential to the present invention. An advantage of the artificial kidney device is that no dialysis fluid will be needed. In a preferred embodiment of this device, the plasma, ultrafiltrate or hemofilter and the electrosorption and decomposition filter are being combined to form a filter package, said filter package comprising an envelop, made from a hemofilter material, surrounding a filter material and electrodes.

Figure 1:
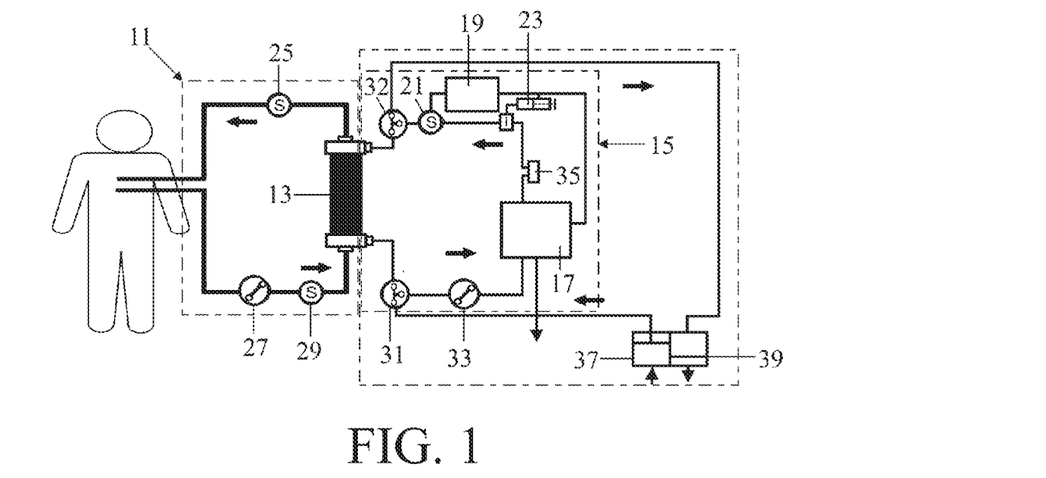

The fluidic scheme of such a device for hemodialysis treatment is depicted in FIG. 1. Blood from a patient is fed via blood lines 11 to a hemofilter at a flow rate of 100-200 ml/min (typically 125 ml/min). Toxins are transferred by the dialyzer membrane 13 (e.g. a high flux filter) to the dialysate circuit. In the dialysate circuit 15, the dialysate is passed through a sorbent unit 17 where the dialysate is being cleansed from toxins via electrosorption and electrocatalytic decomposition.

Here urea, urate, ammonia, creatinine and other toxins with amine-groups are being decomposed and degased. The voltage over each pair of electrodes can be as high as 20 V but in order to limit hydrolysis, the voltage difference should be kept low, typically below 4 V. Other toxins such as the small solutes potassium and phosphate as well as toxic middle molecules as beta2microglobulin and the protein bound toxins such as p-cresol, indoxylsulphate and hyppuric acid are adsorbed in the electrosorption section.

The nanostructured sorption materials herein offer a very large surface area and chemical activity to bind a high load of toxins, typically in the range of 10-50% on weight basis. This purification mode can be operated until the sorption material is saturated with toxins. This depends on the amount of sorbent used. A representative embodiment will comprise 100-500 grams (typically around 150-200 grams) of sorbent, allowing a continuous purification mode to last 6-24 hours. The device can be set into reverse mode by switching the external voltage into its opposite sign in combination with a regeneration fluid. With the reversed voltage, the sorption function changes into a repellent function and the toxins are enforced to unbind and to leave sorbent surface. Hereby the sorbent is being cleaned and regenerated. The released toxins in the compartment are removed by disposing the regeneration fluid.

The quality of the dialysate is being monitored by a control unit 19. This control unit is provided with sensors 21, typically for temperature, conductivity, pH and redox state. The redox sensor 21 is used to safeguard the system for producing oxidative stress. Upon reading, the electrocatalytic decomposition is regulated and if needed the injector system 23 is activated for infusion of a reducing or oxidizing agent.

In order to prevent fluidic overload, excess fluid can be withdrawn from the patient via a seperate line that removes ultrafiltrate from the patient. This can be done continuously (as a drain, typical flow rate 1 ml/min) or discontinuously a few times a day (e.g. 20 ml/min for 20 minutes).

The volume of the disposed ultrafiltrate is typically around 1-2 L per day, the normal amount of excess fluid to be released by a human. The blood circuit 11 further comprises a temperature sensor 25, a blood pump 27 and a temperature pressure air bubble detector 29. The dialysate ciruit further comprises two valves 31, 32, a dyalysate pump 33 and a degasser 35.

Figure 2:
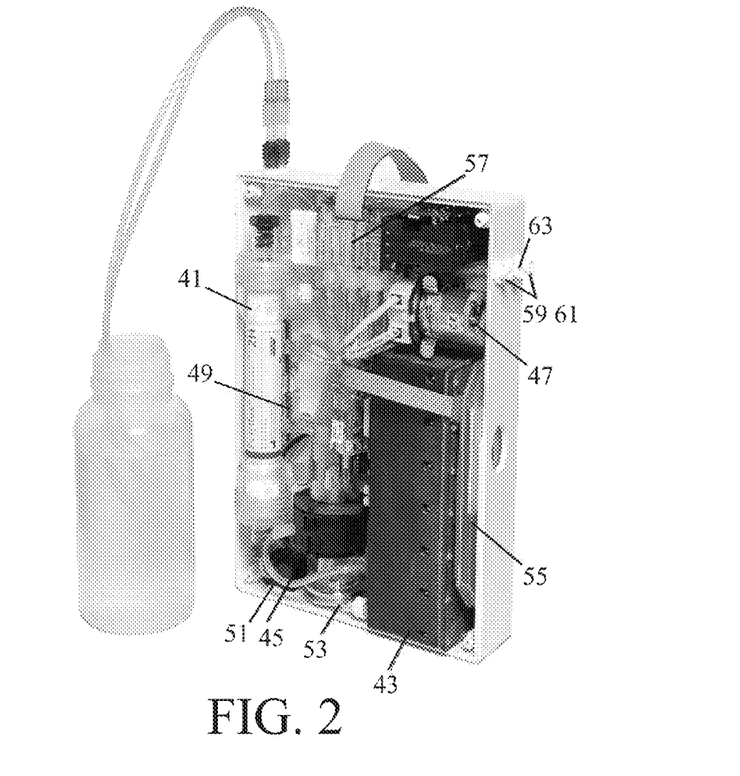

In FIG. 2 a picture is shown of a prototype version that is used for experimental verification. It comprises a hemofilter 41 in order to exchange toxins from the blood to the dialysate and to extract ultrafiltrate. The electrosorption and decomposition unit 43 continuously removes the toxins from the dialysate. Other components such as pumping units 45, 47, degas-unit 55, sensors 49-53 and fluidic valves and injector 57 are indicated in picture 2.

The hemofilter in a device of the present invention is preferably a commercially available hemofilter (e.g. such as produced by Gambro GmbH, Hechingen, Germany or Membrana GmbH, Wuppertal, Germany).

In an alternative embodiment the electrosorption and decomposition filter in a device of the invention may comprise an inlet 59 for receiving patient blood plasma or ultrafiltrate exiting said plasmafilter or hemofilter, and at least one outlet 61, 63 for recovery of purified blood plasma or ultrafiltrate.

A device of the present invention may, in any embodiment, further comprise means for supplementing the (purified) blood plasma or dialysate fluid with at least one substance selected from the group consisting of vitamins such as vitamins A, C, E and B12; minerals such as calcium, sodium and potassium; anticoagulants; bicarbonate to restore the acidose of a patient, anti microbial agents and other medicaments.

Optionally, the device or filter pad may comprise ion exchange systems.

In another aspect, the present invention provides a method for removing toxic substances from blood, comprising using a device according to the present invention.

In another aspect, the present invention provides a method for removing toxic substances from hemodialysis or peritoneal dialysis fluids, comprising using a device according to the present invention.

In another aspect, the present invention provides a method for removing substances from other fluids such as water, e.g. for making drinking water or purifying aquarium water, and for purifying chemicals used in industrial processes as well as removing substances from other biofluids such as urine, milk, bio-analytical fluids, comprising using a device according to the present invention.

The electrosorption and decomposition filter in a device of the present invention may take the form of a filter cartridge, consisting of a rigid or flexible container comprising a set of built-in electrodes and a replaceble filter pad with sorption materials.

This, in another aspect, the present invention may take the form of a device with built-in electrodes connected to a power supply such as a battery or a rectifier, holding an electrosorption and decomposition filter cartridge in contact with these electrodes and comprising a blood plasma separator or hemofilter and a sorption filter pad with sorption materials for extracting ionic solutes and small and middle sized molecules from the blood plasm, ultrafiltrate or dialysate.

In a preferred embodiment therefore, the device for the removal of toxic substances from blood from a patient, comprises a hemofilter and an electrosorption filter, wherein the electrosorption filter removes toxic solutes, small and middle-sized molecules from the blood based, and includes such functions as selective sorption, controlled release and anti-microbial control.

In a most preferred embodiment, the plasmafilter of hemofilter, and electrosorption filter are separate parts. For instance, the plasmafilter or hemofilter may consist of an existing, commercially available plasmafilter or (high flux) hemofilter and the electrosorption filter may consist of a cartridge with built in electrodes. In this cartridge also the sorption material is contained. The sorption material can be held in a porous envelop to form a filter pad.

The device of the present invention can be used for filtering or purification of blood of patients with a (developing) renal failure. In a preferred embodiment, the device takes the form of a wearable artificial kidney device, but can also be embodied in desktop sized equipment or in adapted hemodialysis or peritoneal dialysis equipment.

The artificial kidney is able to perform some of the functions which normally will be done by a properly functioning human or animal kidney, in particular filtering of blood and regulation and control of the content of substances in the blood.

Redox Control and Prevention Chloramines

Chloramines are being formed as a byproduct from the electrocatalytic decomposition. In a solution where next to urea and organic toxins also chloride ions are present, the electrocatalytic decomposition will also interact with the chloride ions leading to oxidation and the formation of chorine (Cl2) and hypochlorite (HOCL) according to the following reactions.

$$2Cl^- > Cl_2 + 2e$$

$$Cl2 + H_2O > HOCl + HCl$$

Hypochlorite in turn may react with ammonia or amines to form chloramines, predominantly monochloramine $NH_2Cl$:

$$NH_3 + HOCl \rightarrow NH_2Cl + H_2O$$

Chloramines provide oxidative stress and this may harm e.g. red blood cells leading to hemolysis. This must be prevented at all times. The safety limit for chloramines is set to max. 0.1 mg/l (ANSI/AMI RD5 standard).

One way of preventing chloramines is to make sure that sufficient sorbent material is present in the sorbent unit itself that is capable of absorbing or eliminating chloramines. Especially activated carbon is very useful in this respect since activated carbon can entrap chloramines and can break down chloramines by catalytic reduction. This is well known in the industry of water purification. It has been found that for a wearable hemodialysis device, a carbon trap of 50-100 grams is sufficient to eliminate all chloramines residues. Other types of carbon within the carbonaceous family such as nanotubes and graphene might show similar or even better capabilities.

Also important in this respect is the choice and size of the electrocatalytic electrodes. It has been found that members of the carbonaceous family such as carbon and graphite tend to produce less chloramines than metal electrodes such as Pt. However the catalytic decomposition of urea and related toxins is also less efficient compared to Pt. This in turn effects the overall design of the system.

In order safeguard the system from producing oxidative stress, a three level safety approach is followed:

(1) depending on the capacity of the electrocatalytic decomposition system and the related production of chloramines, a carbon trap is employed with sufficient capacity to entrap and decompose the formed chloramines. For safety this carbon trap should be overdesigned e.g. with a factor two.

Figure 7:
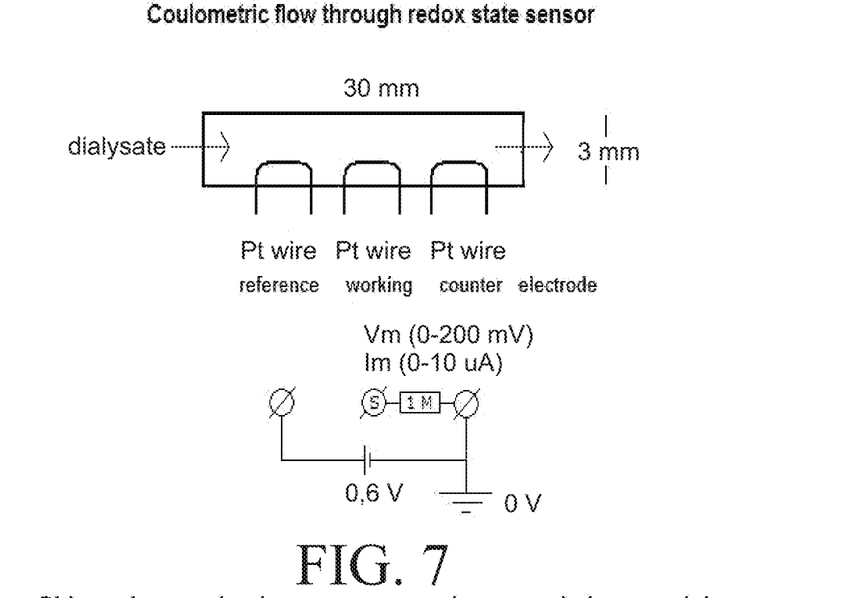
FIG. 7 shows a typical example of a coulometric redox state sensor which can be used to measure the oxidation-reduction potential of the cleansed fluid
Figure 8:
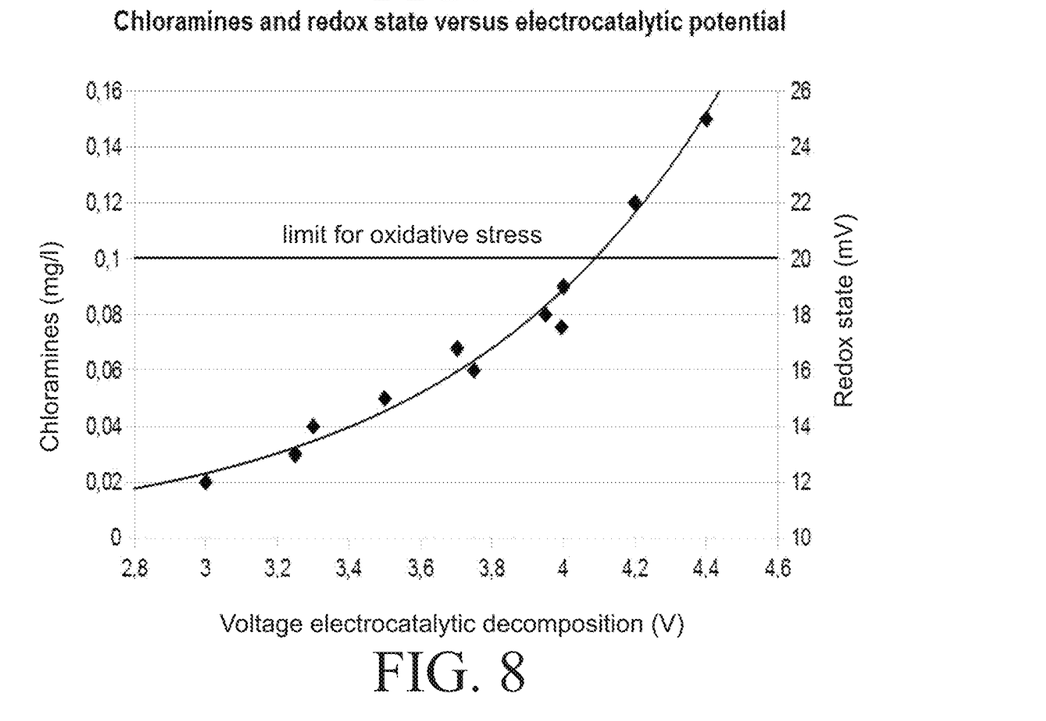
FIG. 8 shows the response of such a sensor upon the presence of chloramines as a byproduct from electrocatalytic decomposition. In order to stay on the safe side for biocompatibility the level of chloramines must be kept below 0.1 mg/l, this corresponds to a redox value of <20 mV for this sensor.

(2) to control the efficiency of the carbon trap over time, the redox state is continuously monitored by means of redox sensor. The redox state is a measure for the level of chloramines. In case the redox state rises and tends to reach the limit value, the intensity of the electrocatalytic decomposition is reduced. This will lower the redox state. A redox state sensor measures the oxidation-reduction potential (ORP) of a fluid. Such a sensor can be a commercially available ORP sensor (usually comprising a Pt-electrode, Ag/AgCl reference electrode and a salt-bridge, see e.g. Mettler Toledo or Vernier) or a flow-through coulometric sensor as depicted in FIG. 7. In FIG. 7 three Pt wires are used for both the reference, working and counter electrode, but other materials such as Au, Ag or Ag/AgCl can also be used. In FIG. 8 the response is shown of such a sensor upon the presence of chloramines (oxidizing agent).

(3) in case of a sudden, unexpected rise in redox state (e.g. due to a break through of chloramines) an injector is activated for the infusion of reducing agent such as vitamin C (ascorbic acid) or similar anti-oxidant. The antioxidant reduces the choramine back to ammonia and chloride ions:

$$C_5H_5O_5CH_2OH + NH_2Cl > C_5H_3O_5CH_2OH + NH_3 + HCl$$

EXPERIMENTAL RESULTS

Example 1: Hemodialysis Performance

Figure 3:
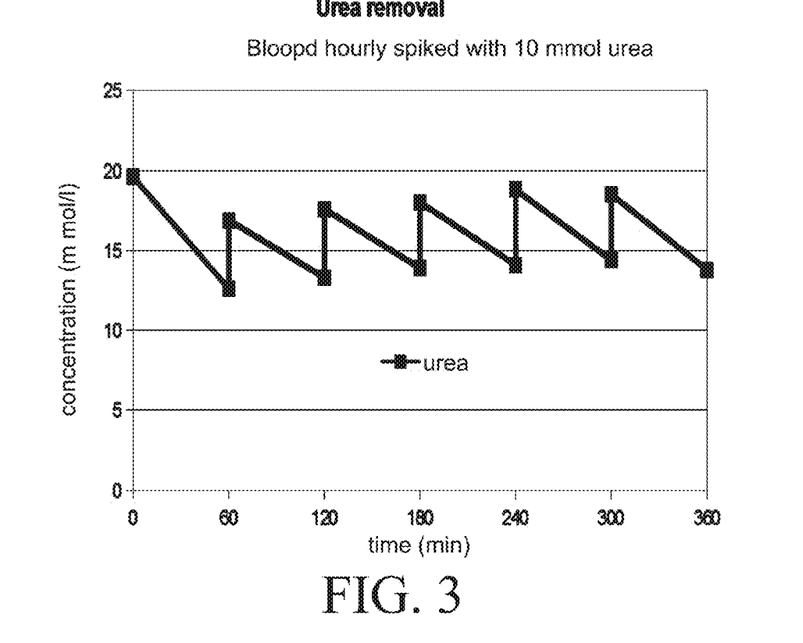
FIG. 3-6 are experimental results obtained with a prototype of the invention and indicate the typical performance in terms of clearance of toxins.
Figure 4:
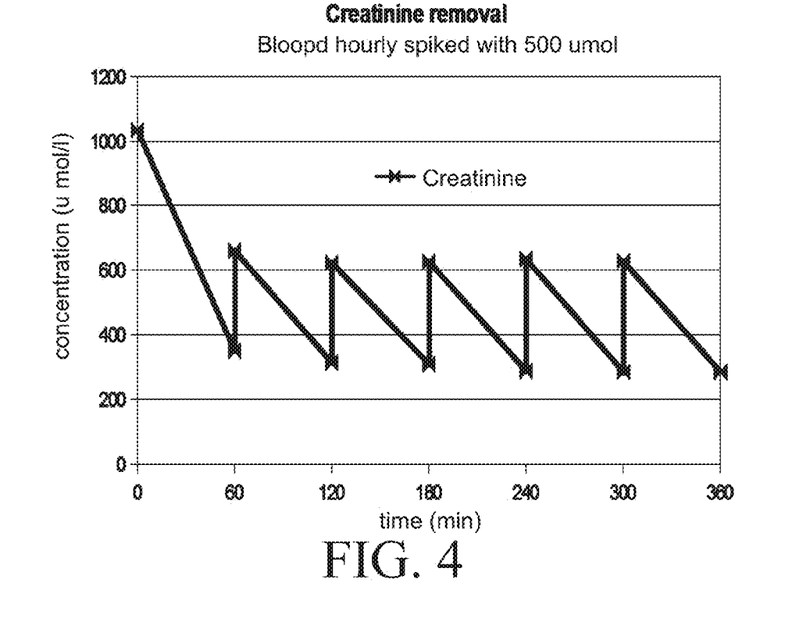
Figure 5:
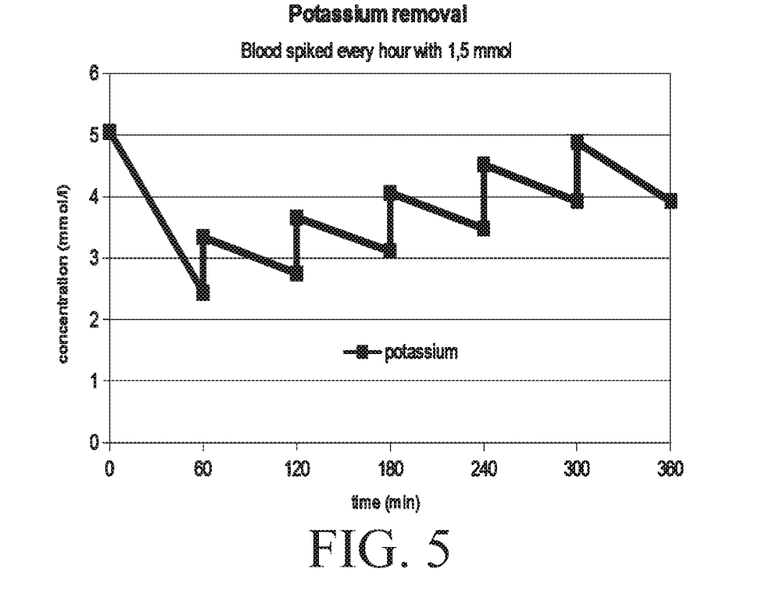
Figure 6:
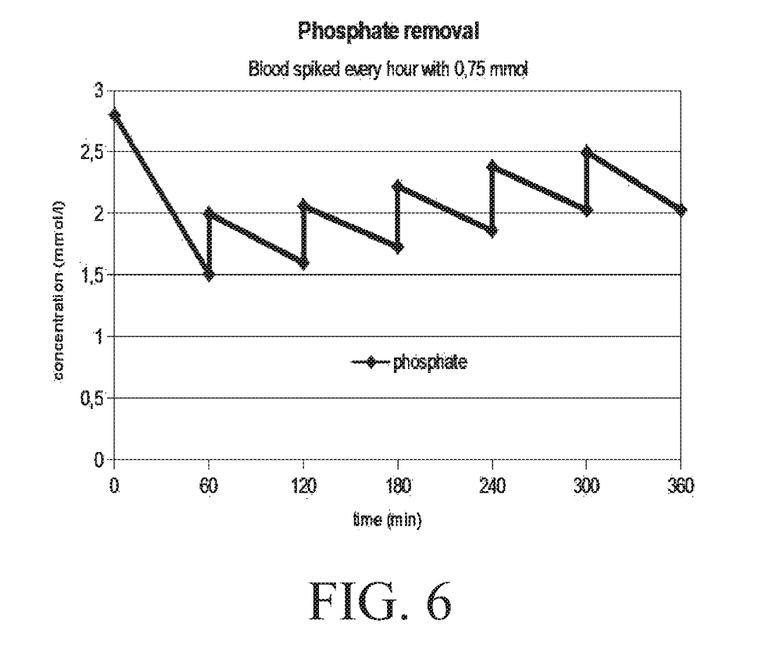

A prototype has been built as depicted in FIG. 2. This setup has been tested in a dynamic test using 1.5 L of animal blood passing a high flux filter at 120 ml/min for dialysis treatment. The dialysate circuit contained 100 ml of dialysate. The electrosorption and decomposition unit was filled with 110 grams of an ion-exchange resin (ps-pvb), 50 grams of a nanostructured FeOOH sorbent and 50 grams of activated carbon. Graphite electrodes were used for the decomposition of urea and related toxins at a voltage of 3.6 V per electrode pair. The total electrode surface amounted to 585 cm². The dialysate flow was set to 45 ml/min. Concentrations in the animal blood were measured every hour. After each hour the blood was spiked with new toxins (urea 10 mmol, potassium 1.5 mmol, phosphate 0.75 mmol, creatinine 0.5 mmol) in order to maintain a representative toxin level. The concentration profiles are depicted in FIG. 3-6, in which:

FIG. 3 shows a diagram of Urea removal from 1.5 L animal blood (cow) with a sorbent unit with 160 g sorbents and 585 cm2 electrodes in a dialysis setup (Gambro 2H filter). Every hour the blood was spiked with 10 mmol urea. Total removed in 6 hours: 60 mmol urea;

FIG. 4 shows a diagram of Creatinine removal from 1.5 L animal blood (cow) with a sorbent unit with 160 g sorbents and 585 cm2 electrodes in a dialysis setup (Gambro 2H filter). Every hour the blood was spiked with 0.5 mmol creatinine. Total removed in 6 hours: 3.7 mmol creatinine;

FIG. 5 shows a diagram of Potassium removal from 1.5 L animal blood (cow) with a sorbent unit with 160 g sorbents and 585 cm2 electrodes in a dialysis setup (Gambro 2H filter). Every hour the blood was spiked with 1.5 mmol potassium. Total removed in 6 hours: 9 mmol potassium; and FIG. 6 shows a diagram of Phosphate removal from 1.5 L animal blood (cow) with a sorbent unit with 160 g sorbents and 585 cm2 electrodes in a dialysis setup (Gambro 2H filter). Every hour the blood was spiked with 0.75 mmol phosphate. Total removed in 6 hours: 5 mmol phosphate.

The overall results are given in the table below.

TABLE

| Hemodialysis experiment: 6 hours dialysis of animal blood | |
| --- | --- |
| Toxin | Total removed in 6 hours (mmol) |
| Urea | 60 |
| Creatinine | 3.7 |
| Potassium | 9 |
| Phosphate | 5 |

FIG. 7 shows an example of a coulometric flow through redox state sensor. It comprises three electrodes: a reference electrode, a working electrode where molecules are being oxidized or reduced and a counter electrode for measuring the amount of molecules that have been oxidized or reduced. In this setup the electrodes are Pt wires, but other geometries and metals (such as Au, Ag, AgCl) are also feasible.

FIG. 8 shows a diagram of Chloramines and redox state versus electrocatalytic potential. As a first safety measure chloramine level is controlled below 0.1 mg/l by means of a redox sensor and a control system that regulates the electrocatalytic decomposition. The threshold value for chloramines is 0.1 mg/l (ANSI/AAMI RD5:2003). In this example (see experiment 1) it means that the voltage of the electrocatalytic decomposition should be kept below 4.1 V.

Figure 9:
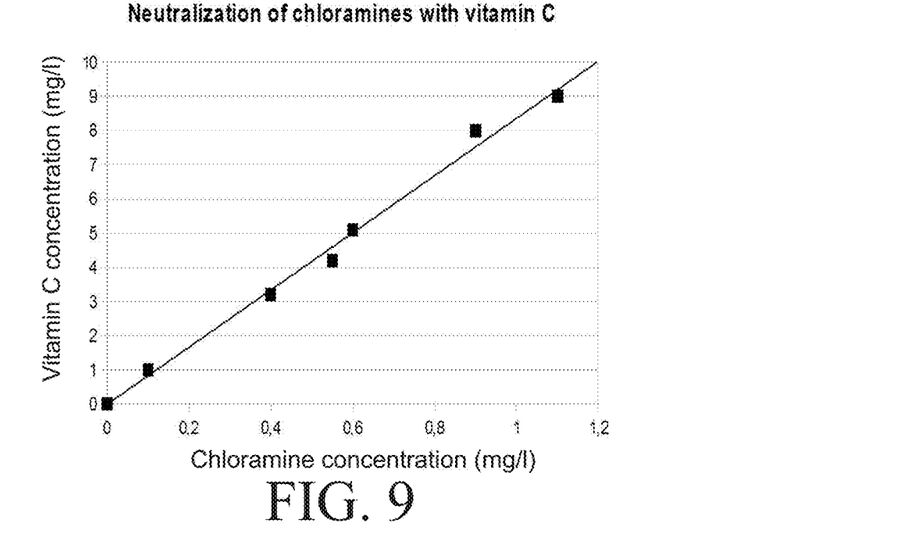
FIG. 9 shows the amount of vitamin C that is needed to neutralize the presence of chloramines in case of a breakout. The anti-oxidant vitamin C will react (reduce) with the chloramines to form harmless chloride ions and amines.

FIG. 9 shows a diagram of Neutralization of chloramines with vitamin C. As a second safety measure infusion of vitamin C (or similar anti-oxidants such as sodium-ascorbate, vitamin E, glutathion) is initiated in case the voltage control mechanism fails to keep the chloramine level below 0.1 mg/l. This figure shows the amount of vitamin C that is needed to fully neutralize the presence of chloramines.

Example 2: Prevention of Oxidative Stress

The prototype as described in example 1 was also used to verify the prevention of oxidative stress. Two oxidative stress tests have been performed:

(1) MDA test: Lipid peroxidation is a well-defined mechanism of cellular damage in animals and plants. Lipid peroxides are unstable indicators of oxidative stress in cells that decompose to form more complex and reactive compounds such as Malondialdehyde (MDA) and 4-hydroxynonenal (4-HNE), natural byproducts of lipid peroxidation. Oxidative modification of lipids can be induced in vitro by a wide array of pro-oxidant agents and occurs in vivo during aging and in certain disease conditions. Measuring the end products of lipid peroxidation is one of the most widely accepted assays for oxidative damage. These aldehydic secondary products of lipid peroxidation are generally accepted markers of oxidative stress.

Figure 10:
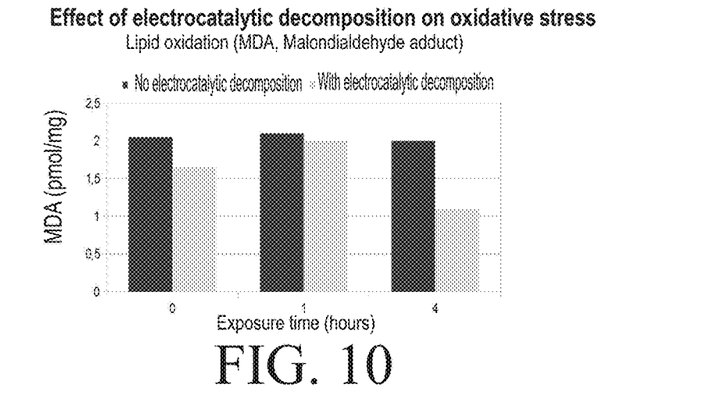
FIGS. 10 and 11 show experimental results with respect to the prevention of oxidative stress measured with a MDA test (lipid oxidation) and AOPP test (protein oxidation)
Figure 11:
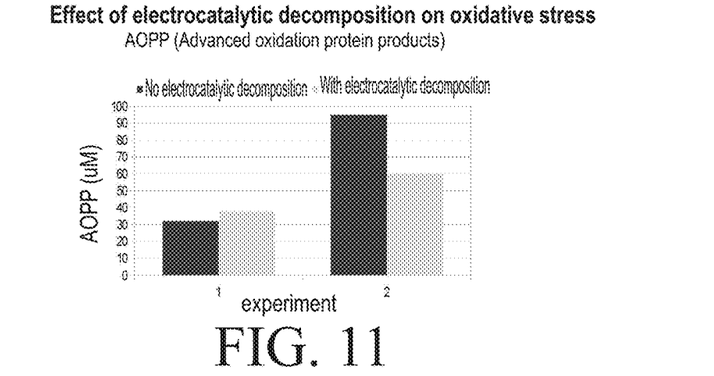

(2) AOPP test: Advanced Oxidation Protein Products (AOPP) are uremic toxins created during oxidative stress through the reaction of chlorinated oxidants, such as chloramines and hypochlorous acid, with plasma proteins. AOPPs are structurally similar to Advanced Glycation End-Product (AGE) proteins and exert similar biological activities. AOPPs are elevated in patients with renal complications, atherosclerosis, diabetes mellitus, systemic sclerosis, as well as HIV-positive patients. Human Serum Albumin (HSA) treated with HOCl and AOPP generated in vivo can ignite oxidative reactions in both neutrophils and monocytes, which indicates both can be used as true mediators of inflammation The results of these tests are depicted in FIGS. 10 (MDA test) and 11 (AOPP test) in which:

FIG. 10 shows a diagram of the effect of electrocatalytic decomposition on oxidative stress in which the Oxidative stress is measured according to the MDA test (lipid oxidation, formation of malondialdehyde adduct) at conditions as described in experiment 1. Electrocatalytic decomposition does not produce oxidative stress. Tendency is even to lower the oxidative stress (probably due to the presence of carbon in the dialysate circuit); and FIG. 11 shows a diagram of the effect of electrocatalytic decomposition on oxidative stress in which the Oxidative stress is measured according to the AOPP test (advanced protein oxidation formation) at conditions as described in experiment 1. Electrocatalytic decomposition does not produce oxidative stress.

As is evident from these figures, the measures that were taken to prevent oxidative stress (carbon trap and voltage control on the electrocatalytic decomposition) appeared to be successful. No oxidative stress due to electrocatalytical decomposition could be detected.

The invention claimed is:

1. A device for the removal of toxic substances from dialysate fluid, blood, blood plasma or ultra filtrate, comprising:
   i) a housing having an inlet for entry of dialysate fluid, blood, blood plasma or ultrafiltrate into said housing, an outlet for the removal of purified dialysate fluid, blood, blood plasma or ultrafiltrate and excess fluid from said housing, and a conduit connecting said inlet with said outlet
   ii) an electrocatalytic decomposition filter for removing toxins, toxic solutes, toxic small and middle-sized molecules and protein bound toxins from the dialysate fluid, blood, bloodplasma or ultrafiltrate, said electrocatalytic decomposition filter being contained in said conduit such that said dialysate fluid, blood, blood plasma or ultrafiltrate must pass through said electrocatalytic decomposition filter when flowing from said inlet to said outlet and said electrocatalytic decomposition filter comprising:

a) a set of electrodes with an electrocatalytic surface for decomposition and gasification of toxins via electro-oxidation
b) or a set of electrodes that are in direct electrical contact with porous materials that have been coated with electrocatalytic material
c) power source to provide the electrodes with an electrical charge in order to activate the electrocatalytic electrode surface or the electrocatalytic material
d) an electronic means to control and switch the electrical charge on the electrodes in view of resorbing and release of toxins and to prevent built-up of deposits on the electrodes, iii) an electrosorption filter for removing toxins, toxic solutes, toxic small and middle-sized molecules and protein bound toxins from the dialysate fluid, blood, blood plasma or ultrafiltrate, said electrosorption filter being contained in said conduit such that said dialysate fluid, blood, blood plasma or ultrafiltrate must pass through said electrosorption filter when flowing from said inlet to said outlet and said electrosorption filter comprising:
a) a nanostructured sorption material;
b) a set of electrodes coated with or in electrical contact with the sorption material;
c) a power source to provide the electrodes with an electrical charge and generate an electrical field strength in the sorption medium;
d) a sensor unit for monitoring the quality of the cleansed dialysate fluid, blood, blood plasma or ultrafiltrate and a control system to correct and adjust the quality of the cleansed dialysate fluid, blood, blood plasma or ultrafiltrate, wherein the sensor unit is configured for monitoring the redox state and the electrocatalytic decomposition rate of the cleansed dialysate fluid, blood, blood plasma or ultrafiltrate and the control system is configured for controlling infusion of a reducing agent to correct and adjust the cleansed dialysate fluid, blood, blood plasma or ultrafiltrate to prevent oxidative stress wherein the electrodes are made from carbonaceous material.

2. Device according to claim 1, wherein the electrosorption filter and electrocatalytic decomposition filter are combined into one filter compartment wherein the sorption material is contained in between the electrocatalytic electrodes.

3. Device according to claim 2, wherein said electrocatalytic decomposition and electrosorption filter is provided in the form of a cartridge with said electrodes coated with said sorption material or with said electrodes surrounded by a porous envelop containing said sorption material.

4. Device according to claim 2, wherein said electrocatalytic decomposition and electrosorption filter is combined with a permeable envelop to form a filter pad comprising an envelop surrounding a filter pad contents, wherein the envelop of said pad comprises a permeable membrane and the contents of said pad comprise said sorption material.

5. Device according to claim 4, further comprising a hemofilter for separating patient ultrafiltrate from patient blood cells or to allow blood-dialysate toxin exchange in a dialysis setup, and a plasmafilter and said electrosorption filter are combined to form a filter pad wherein a permeable membrane is formed by said plasmafilter.

6. Device according to claim 2, wherein said device further comprises a plasmafilter for separating patient blood plasma from patient blood cells.

7. Device according to claim 2, wherein said device further comprises a hemofilter for separating patient ultrafiltrate from patient blood cells or to allow blood-dialysate toxin exchange in a dialysis setup.

8. Device according to claim 2, wherein said device further comprises an electrosorption filter for removing toxins, small and middle-sized molecules from the patient blood plasma.

9. Device according to claim 2, wherein said device further comprises means for supplementing said dialysate fluid and/or said (purified) blood plasma with at least one substance selected from the group consisting of vitamins, minerals, anticoagulants, anti microbial agents and other medicaments.

10. Device according to claim 2, wherein said device further comprises ion exchange systems.

11. Device according to claim 2, wherein the sorption materials are being regenerated with a regeneration fluid in combination with a reversed voltage mode on the electrodes, and that optionally the voltage of the external source is electronically regulated depending on the reading of the sensor system and/or can be reversed into opposite values in order to repel and to release toxins, unwanted deposits and to regenerate the sorption materials.

12. Device according to claim 1, wherein said device further comprises a plasmafilter for separating patient blood plasma from patient blood cells.

13. Device according to claim 12, further comprising an electrosorption filter for removing toxins, small and middle-sized molecules from the patient blood plasma, said hemofilter and a electrosorption filter being combined to form a filter pad wherein a permeable membrane is formed by said hemofilter.

14. Device according to claim 1, wherein said device further comprises a hemofilter for separating patient ultrafiltrate from patient blood cells or to allow blood-dialysate toxin exchange in a dialysis setup.

15. Device according to claim 1, wherein said device further comprises an electrosorption filter for removing toxins, small and middle-sized molecules from the patient blood plasma.

16. Device according to claim 1, wherein said device further comprises means for supplementing said dialysate fluid and/or said (purified) blood plasma with at least one substance selected from the group consisting of vitamins, minerals, anticoagulants, anti microbial agents and other medicaments.

17. Device according to claim 1, wherein said device further comprises ion exchange systems.

18. Device according to claim 1, wherein the sorption materials are being regenerated with a regeneration fluid in combination with a reversed voltage mode on the electrodes, and that optionally the voltage of the external source is electronically regulated depending on the reading of the sensor system and/or can be reversed into opposite values in order to repel and to release toxins, unwanted deposits and to regenerate the sorption materials.

* * * * *